(12) United States Patent
Dell 'Orco et al.

(10) Patent No.: US 7,645,338 B2
(45) Date of Patent: *Jan. 12, 2010

(54) CRYSTALLINE DERIVATIVES OF (E)-2-(5-CHLOROTHIEN-2-YL)-N-{(3S)-1-[(1S)-1-METHYL-2-MORPHOLIN-4-YL-2-OXOETHYL]-2-OXOPYRROLIDIN-3-YL} ETHENESULFONAMIDE

(75) Inventors: Philip C. Dell 'Orco, King of Prussia, PA (US); Henry Anderson Kelly, Stevenage (GB); Gita Punjabhai Shah, Stevenage (GB); Nigel Stephen Watson, Stevenage (GB); Robert John Young, Stevenage (GB)

(73) Assignee: Glaxo Group Limited, Greenford (GB)

( * ) Notice: Subject to any disclaimer, the term of this patent is extended or adjusted under 35 U.S.C. 154(b) by 259 days.

This patent is subject to a terminal disclaimer.

(21) Appl. No.: 10/537,645

(22) PCT Filed: Dec. 4, 2003

(86) PCT No.: PCT/EP03/13800

§ 371 (c)(1),
(2), (4) Date: Nov. 16, 2005

(87) PCT Pub. No.: WO2004/052878

PCT Pub. Date: Jun. 24, 2004

(65) Prior Publication Data

US 2006/0124049 A1    Jun. 15, 2006

(30) Foreign Application Priority Data

Dec. 6, 2002    (GB) .................. 0228533.6

(51) Int. Cl.
*C30B 29/54* (2006.01)
(52) U.S. Cl. ............................ 117/68; 117/69; 117/70
(58) Field of Classification Search .................. 117/68, 117/69, 70, 935
See application file for complete search history.

(56) References Cited

U.S. PATENT DOCUMENTS

| 6,281,227 B1 * | 8/2001 | Choi-Sledeski et al. ..... 514/307 |
| 6,602,864 B1 * | 8/2003 | Choi-Sledeski et al. 514/210.02 |
| 7,084,139 B2 * | 8/2006 | Chan et al. ............... 514/235.5 |
| 7,179,835 B2 * | 2/2007 | Borthwick et al. .......... 514/423 |

FOREIGN PATENT DOCUMENTS

| WO | 02/100830 | 12/2002 |
| WO | 02/100886 | 12/2002 |

* cited by examiner

*Primary Examiner*—Robert M Kunemund
(74) *Attorney, Agent, or Firm*—Bonnie L. Deppenbrock (57) ABSTRACT

The present invention includes (E)-2-(5-Chlorothien-2-yl)-N-{(3S)-1-[(1S)-1-methyl-2-morpholin-4-yl-2-oxoethyl]-2-oxopyrrolidin-3-yl}ethenesulfonamide in substantially crystalline form, pharmaceutical formulations thereof, processes for preparing it, and its use in medicine, particularly use in the amelioration of a clinical condition for which a Factor Xa inhibitor is indicated.

10 Claims, 2 Drawing Sheets

Figure 1. X-Ray Powder Diffractogram of substantially crystalline Example 1.

Figure 2. X-Ray Powder Diffractogram of substantially crystalline Example 2.

CRYSTALLINE DERIVATIVES OF (E)-2-(5-CHLOROTHIEN-2-YL)-N-{(3S)-1-[(1S)-1-METHYL-2-MORPHOLIN-4-YL-2-OXOETHYL]-2-OXOPYRROLIDIN-3-YL} ETHENESULFONAMIDE

This application is filed pursuant to 35 U.S.C. §371 as a U.S. National Phase Application of International Application No. PCT/EP2003/013800 filed Dec. 4, 2003, which claims priority from GB 0228533.6 filed Dec. 6, 2002, each incorporated herein by reference.

The present invention relates to crystalline derivatives of an oxopyrrolidine compound and its use in medicine. More particularly, the invention is concerned with a substantially crystalline form of (E)-2-(5-chlorothien-2-yl)-N-{(3S)-1-[(1S)-1-methyl-2-morpholin-4-yl-2-oxoethyl]-2-oxopyrrolidin-3-yl}ethenesulfonamide, pharmaceutical formulations thereof, processes for preparing it, and its use in medicine, particularly use in the amelioration of a clinical condition for which a Factor Xa inhibitor is indicated.

Factor Xa is a member of the trypsin-like serine protease class of enzymes. It is a key enzyme in the coagulation cascade. A one-to-one binding of Factors Xa and Va with calcium ions and phospholipid converts prothrombin into thrombin. Thrombin plays a central role in the mechanism of blood coagulation by converting the soluble plasma protein, fibrinogen, into insoluble fibrin. The insoluble fibrin matrix is required for the stabilisation of the primary hemostatic plug. Many significant disease states are related to abnormal hemostasis. With respect to the coronary arterial vasculature, abnormal thrombus formation due to the rupture of an established atherosclerotic plaque is the major cause of acute myocardial infarction and unstable angina. Both treatment of an occlusive coronary thrombus by thrombolytic therapy and percutaneous transluminal coronary angioplasty (PTCA) are often accompanied by an acute thrombotic reclosure of the affected vessel which requires immediate resolution. With respect to the venous vasculature, a high percentage of patents undergoing major surgery in the lower extremities or the abdominal area suffer from thrombus formation in the venous vasculature which can result in reduced blood flow to the affected extremity and a pre-disposition to pulmonary embolism. Disseminated intravascular coagulopathy commonly occurs within both vascular systems during septic shock, certain viral infections and cancer and is characterised by the rapid consumption of coagulation factors and systemic coagulation which results in the formation of life-threatening thrombi occurring throughout the vasculature leading to widespread organ failure.

Beyond its direct role in the formation of fibrin rich blood clots, thrombin has been reported to have profound bioregulatory effects on a number of cellular components within the vasculature and blood, (Shuman, M. A., Ann. NY Acad. Sci., 405: 349 (1986)).

A Factor Xa inhibitor may be useful in the treatment of acute vascular diseases such as acute coronary syndromes (for example primary and secondary prevention of myocardial infarction and unstable angina and treatment of pro-thrombotic sequalae associated with myocardial infarction or heart failure), thromboembolism, acute vessel closure associated with thrombolytic therapy and percutaneous transluminal coronary angioplasty, transient ischemic attacks, pulmonary embolism, deep vein thrombosis, peripheral arterial occlusion, prevention of vessel luminal narrowing (restenosis), and the prevention of thromboembolic events associated with atrial fibrillation, e.g. stroke. Factor Xa inhibitors may also be useful in preventing thrombosis and complications in patients genetically predisposed to arterial thrombosis or venous thrombosis and patients that have a disease-associated predisposition to thrombosis (e.g. type 2 diabetics). Thrombin has been reported to contribute to lung fibroblast proliferation, thus, Factor Xa inhibitors could be useful for the treatment of some pulmonary fibrotic diseases. Factor Xa inhibitors could also be useful in the treatment of tumour metastasis, by suppressing coagulation and thus preventing fibrin deposition and its concommittant facilitation of metastasis. A Factor Xa inhibitor may also have utility as an anti-inflammatory agent through its inhibition of FXa mediated activation of protease-activated receptors (PAR 1-4). A Factor Xa inhibitor may also have utility as an anti-atherosclerotic agent through the suppression of platelet-activation. Thrombin can induce neurite retraction and thus Factor Xa inhibitors may have potential in neurogenerative diseases such as Parkinson's and Alzheimer's disease. Factor Xa inhibitors may also have utility as anticoagulant agents in connection with the preparation, storage, fractionation or use of whole blood. They have also been reported for use in conjunction with thrombolytic agents, thus permitting the use of a lower dose of thrombolytic agent.

(E)-2-(5-Chlorothien-2-yl)-N-{(3S)-1-[(1S)-1-methyl-2-morpholin-4-yl-2-oxoethyl]-2-oxopyrrolidin-3-yl}ethenesulfonamide is a FXa inhibitor disclosed in WO02/100886 and WO02/100830, incorporated herein by reference, in a substantially amorphous form. (E)-2-(5-Chlorothien-2-yl)-N-{(3S)-1-[(1S)-1-methyl-2-morpholin-4-yl-2-oxoethyl]-2-oxopyrrolidin-3-yl}ethenesulfonamide has the structure shown below:

(I)

SUMMARY OF THE INVENTION

We have now found that (E)-2-(5-chlorothien-2-yl)-N-{(3S)-1-[(1S)-1-methyl-2-morpholin-4-yl-2-oxoethyl]-2-oxopyrrolidin-3-yl}ethenesulfonamide can be obtained in a substantially crystalline form. Thus there is provided in a first aspect of the invention (E)-2-(5-chlorothien-2-yl)-N-{(3S)-1-[(1S)-1-methyl-2-morpholin-4-yl-2-oxoethyl]-2-oxopyrrolidin-3-yl}ethenesulfonamide in substantially crystalline form.

Further aspects of the invention are:

A pharmaceutical composition comprising (E)-2-(5-chlorothien-2-yl)-N-{(3S)-1-[(1S)-1-methyl-2-morpholin-4yl-2-oxoethyl]-2-oxopyrrolidin-3-yl}ethenesulfonamide in substantially crystalline form together with a pharmaceutical carrier and/or excipient.

(E)-2-(5-chlorothien-2-yl)-N-{(3S)-1-[(1S)-1-methyl-2-morpholin-4-yl-2-oxoethyl]-2-oxopyrrolidin-3-yl}ethenesulfonamide in substantially crystalline form for use in therapy.

Use of (E)-2-(5-chlorothien-2-yl)-N-{(3S)-1-[(1S)-1-methyl-2-morpholin-4-yl-2-oxoethyl]-2-oxopyrrolidin-3-yl}ethenesulfonamide in substantially crystalline form for the manufacture of a medicament for the treatment of a patient suffering from a condition susceptible to amelioration by a Factor Xa inhibitor.

A method of treating a patient suffering from a condition susceptible to amelioration by a Factor Xa inhibitor comprising administering a therapeutically effective amount of (E)-2-(5-chlorothien-2-yl)-N-{(3S)-1-[(1S)-1-methyl-2-morpholin-4-yl-2-oxoethyl]-2-oxopyrrolidin-3-yl}ethenesulfonamide in substantially crystalline form.

DESCRIPTION OF THE INVENTION

The substantially crystalline form of E)-2-(5-chlorothien-2-yl)-N-{(3S)-1-[(1S)-1-methyl-2-morpholin-4-yl-2-oxoethyl]-2-oxopyrrolidin-3-yl}ethenesulfonamide may be obtained by crystallisation under certain conditions in the form of needle and/or lath shaped particles, up to 250 microns in length, as described below. There is thus provided in a further aspect of the invention, substantially crystalline (E)-2-(5-chlorothien-2-yl)-N-{(3S)-1-[(1S)-1-methyl-2-morpholin-4-yl-2-oxoethyl]-2-oxopyrrolidin-3-yl}ethenesulfonamide in the form of needle-shaped crystals. There is also provided in a further aspect of the invention, substantially crystalline (E)-2-(5-chlorothien-2-yl)-N-{(3S)-1-[(1S)-1-methyl-2-morpholin-4-yl-2-oxoethyl]-2-oxopyrrolidin-3-yl}ethenesulfonamide in the form of lath-shaped crystals. There is also provided in a further aspect of the invention, substantially crystalline (E)-2-(5-chlorothien-2-yl)-N-{(3S)-1-[(1S)-1-methyl-2-morpholin-4-yl-2-oxoethyl]-2-oxopyrrolidin-3-yl}ethenesulfonamide in the form of a mixture of needle-shaped and lath-shaped crystals. Preferably, the crystals are up to 250 microns in length. However, it will be appreciated that alternative crystal habits under certain circumstances can be formed. It is therefore to be understood that all such alternative crystal habits are within the scope of the present invention.

As used herein, the term "needle-shaped" means a needle-like prism. This shape is also known as "acicular". Preferably needle-shaped crystals are up to 250 microns in length.

As used herein, the term "lath-shaped" means a blade or spatula shaped crystal, in other words a flattened acicular shape. Preferably, lath-shaped crystals are up to 400 microns in length. More preferably, lath-shaped crystals are up to 250 microns in length.

Substantially crystalline (E)-2-(5-chlorothien-2-yl)-N-{(3S)-1-[(1S)-1-methyl-2-morpholin-4-yl-2-oxoethyl]-2-oxopyrrolidin-3-yl}ethenesulfonamide has a melting point onset of 163-165° C. There is thus provided in a further aspect of the invention, (E)-2-(5-chlorothien-2-yl)-N-{(3S)-1-[(1S)-1-methyl-2-morpholin-4-yl-2-oxoethyl]-2-oxopyrrolidin-3-yl}ethenesulfonamide in substantially crystalline form having a melting point onset measured by DSC (±0.5° C.) of: 160° C. or greater, preferably in the range 161-167° C., more preferably in the range 163-165° C.

A sample of substantially crystalline (E)-2-(5-chlorothien-2-yl)-N-{(3S)-1-[(1S)-1-methyl-2-morpholin-4-yl-2-oxoethyl]-2-oxopyrrolidin-3-yl}ethenesulfonamide, prepared as described hereinafter, gave the X-ray powder diffraction patterns of FIG. 1 and FIG. 2. The X-ray diffraction pattern is unique to the crystalline form. The substantially crystalline form exhibits a diffraction pattern with a unique set of diffraction peaks which can be expressed in 2 theta angles (°), d-spacings (Å) and/or relative peak intensities.

2 Theta diffraction angles and corresponding d-spacing values account for positions of various peaks in the X-ray diffraction pattern. D-spacing values are calculated with observed 2 theta angles and copper Kα1 wavelength using the Bragg equation. Slight variations in observed 2 theta angles and d-spacings are expected based on the specific diffractometer employed and the analyst's sample preparation technique. More variation is expected for the relative peak intensities. Identification of the exact crystal form of a compound should be based primarily on observed 2 theta angles or d-spacings with lesser importance place on relative peak intensities. To identify substantially crystalline (E2-(5-chlorothien-2-yl)-N-{(3S)-1-[(1S)-1-methyl-2-morpholin-4-yl-2-oxoethyl]-2-oxopyrrolidin-3-yl}ethenesulfonamide, the characteristic 2 theta angle peak occurs at 18.3±0.1 degrees, or 4.8±0.1 Å d-spacing. In one aspect of the invention, the characteristic 2 theta angle peak occurs at 18.39 degrees, or 4.82 Å d-spacing.

Although one skilled in the art can identify substantially crystalline (E)-2-(5-chlorothien-2-yl)-N-{(3S)-1-[(1S)-1-methyl-2-morpholin-4-yl-2-oxoethyl]-2-oxopyrrolidin-3-yl}ethenesulfonamide from the characteristic 2 theta angle peak at 18.3±0.1, e.g. 18.39 degrees, in some circumstances it may be desirable to rely upon multiple 2 theta angles or multiple d-spacings for the identification of substantially crystalline (E)-2-(5-chlorothien-2-yl)-N-{(3S)-1-[(1S)-1-methyl-2-morpholin-4-yl-2-oxoethyl]-2-oxopyrrolidin-3-yl}ethenesulfonamide. Substantially crystalline (E)-2-(5-chlorothien-2-yl)-N-{(3S)-1-[(1S)-1-methyl-2-morpholin-4-yl-2-oxoethyl]-2-oxopyrrolidin-3-yl}ethenesulfonamide can also be identified by the presence of multiple characteristic 2 theta angle peaks including two, three, or all four of the 2 theta angles which are reasonably characteristic of this particular crystalline form. These peaks occur at the following positions, expressed in 2 theta angles (±0.1 degrees): 9.1-9.2, 16.0-16.1, 18.0-18.2, 18.3-18.4 degrees. In one embodiment at least one of the foregoing 2 theta angles are employed to identify substantially crystalline (E)-2-(5chlorothien-2-yl)-N-{(3S)-1-[(1S)-1-methyl-2-morpholin-4-yl-2-oxoethyl]-2-oxopyrrolidin-3-yl}ethenesulfonamide.

In one particular aspect of the invention, the peaks occur at the following positions, expressed in 2 theta angles (±0.1 degrees): 9.21, 13.79, 16.11, 18.11, 18.39 degrees. At least one, preferably two, more preferably 3, even more preferably 4, most preferably 5, of the foregoing 2 theta angles are employed to identify substantially crystalline (E)-2-(5-chlorothien-2-yl)-N-{(3S)-1-[(1S)-1-methyl-2-morpholin-4-yl-2-oxoethyl]-2-oxopyrrolidin-3-yl}ethenesulfonamide.

In another particular aspect of the invention, the peaks occur at the following positions, expressed in 2 theta angles (±0.1 degrees): 9.1, 16.0, 18.0, 18.3 degrees.

At least one, preferably two, more preferably 3, most preferably 4, of the foregoing 2 theta angles are employed to identify substantially crystalline (E)-2-(5-chlorothien-2-yl)-N-{(3S)-1-[(1S)-1-methyl-2-morpholin-4-yl-2-oxoethyl]-2-oxopyrrolidin-3-yl}ethenesulfonamide.

Some margin of error is present in each of the 2 theta angle assignments and d-spacings reported above. The error in determining d-spacings decreases with increasing diffraction scan angle or decreasing d-spacing. The margin of error in the foregoing 2 theta angles is approximately ±0.1 degrees, preferably ±0.05 degrees, for each of the foregoing peak assignments. The margin of error in d-spacing values is approximately ±0.1 Angstroms, preferably ±0.05 Angstroms.

Since some margin of error is possible in the assignment of 2 theta angles and d-spacings, the preferred method of comparing X-ray powder diffraction patterns in order to identify a particular crystalline form is to overlay the X-ray powder diffraction pattern of the unknown form over the X-ray powder diffraction pattern of a known form. For example, one skilled in the art can overlay an X-ray powder diffraction pattern of an unidentified form of (E)-2-(5-chlorothien-2-yl)-N-{(3S)-1-[(1S)-1-methyl-2-morpholin-4-yl-2-oxoethyl]-2-oxopyrrolidin-3-yl}ethenesulfonamide, obtained using the methods described herein, over FIG. 1 or FIG. 2 and readily determine whether the X-ray diffraction pattern of the unidentified form is substantially the same as the X-ray powder diffraction pattern of substantially crystalline (E)-2-(5-chlorothien-2-yl)-N-{(3S)-1-[(1S)-1-methyl-2-morpholin-4-yl-2-oxoethyl]-2-oxopyrrolidin-3-yl}ethenesulfonamide. If the X-ray powder diffraction pattern is substantially the same as FIG. 1 or FIG. 2, the previously unknown form can be readily and accurately identified as substantially crystalline (E)-2-(5chlorothien-2-yl)-N-{(3S)-1-[(1S)-1-methyl-2-morpholin-4-yl-2-oxoethyl]-2-oxopyrrolidin-3-yl}ethenesulfonamide.

Although 2 theta angles or d-spacings are the primary method of identifying a particular crystalline form, it may be desirable to also compare relative peak intensities. As noted above, relative peak intensities may vary depending upon the specific diffractometer employed and the analyst's sample preparation technique. The peak intensities are reported as intensities relative to the peak intensity of the strongest peak. The intensity units on the X-ray diffraction plot are counts/sec. The absolute counts=counts/time×count time=counts/sec×10 sec.

As used herein, the term "substantially crystalline form" means that it is substantially free of amorphous form (E)-2-(5chlorothien-2-yl)-N-{(3S)-1-[(1S)-1-methyl-2-morpholin-4yl-2-oxoethyl]-2-oxopyrrolidin-3-yl}ethenesulfonamide. By "substantially free" is meant containing less than 50% of the amorphous form, preferably less than 20% of the amorphous form, more preferably less than 10% of the amorphous form, more preferably less than 5% of the amorphous form, even more preferably less than 2% of the amorphous form, most preferably less than 1% of the amorphous form.

As used herein, the term "substantially amorphous form" means amorphous form (E)-2-(5-chlorothien-2-yl)-N-{(3S)-1-[(1S)-1-methyl-2-morpholin-4-yl-2-oxoethyl]-2-oxopyrrolidin-3-yl}ethenesulfonamide which may contain up to 10% crystalline form (E)-2-(5-chlorothien-2-yl)-N-{(3S)-1-[(1S)-1-methyl-2-morpholin-4-yl-2-oxoethyl]-2-oxopyrrolidin-3-yl}ethenesulfonamide but preferably contains less than 5% of the crystalline form, more preferably less than 3% of the crystalline form, even more preferably less than 2% of the crystalline form, most preferably less than 1% of the crystalline form.

(E)-2-(5-Chlorothien-2-yl)-N-{(3S)-1-[(1S)-1-methyl-2-morpholin-4-yl-2-oxoethyl]-2-oxopyrrolidin-3-yl}ethenesulfonamide contains chiral (asymmetric) centres, see*in formula (I). The individual stereoisomers (enantiomers and diastereoisomers) and mixtures of these are within the scope of the present invention. Preferably, the stereochemistry is (S) at the 3-position on the 2-oxopyrrolidine ring. Preferably, the stereochemistry is (S) at the 1-position on the oxoethyl group.

The present invention also provides a method for the preparation of (E)-2-(5-chlorothien-2-yl)-N-{(3S)-1-[(1S)-1-methyl-2-morpholin-4-yl-2-oxoethyl]-2-oxopyrrolidin-3-yl}ethenesulfonamide in substantially crystalline form, which method comprises crystallisation of (E)-2-(5-chlorothien-2-yl)-N-{(3S)-1-[(1S)-1-methyl-2-morpholin-4-yl-2-oxoethyl]-2-oxopyrrolidin-3-yl}ethenesulfonamide from an organic solution, optionally in the presence of water. In general, (E)-2-(5-chlorothien-2-yl)-N-{(3S)-1-[(1S)-1-methyl-2-morpholin-4-yl-2-oxoethyl]-2-oxopyrrolidin-3-yl}ethenesulfonamide is dissolved in an organic solvent, for example an aromatic hydrocarbon (e.g. toluene), a cycloalkane (e.g. cyclohexane), an ester (e.g. ethyl acetate), an alcohol (e.g. ethanol, methanol or propan-2-ol), or a ketone (e.g. acetone), preferably, a ketone (e.g. acetone) or a cycloalkyl (e.g. cyclohexane), more preferably cyclohexane, preferably at elevated temperature e.g. 50-70° C., and optionally water is added as a counter-solvent. Crystallisation is carried out by reducing the temperature of the solution, preferably to between room temperature and 0° C., more preferably 0-5° C. In a preferred aspect of the invention, the crystals of (E)-2-(5-chlorothien-2-yl)-N-{(3S)-1-[(1S)-1-methyl-2-morpholin-4-yl-2-oxoethyl]-2-oxopyrrolidin-3-yl}ethenesulfonamide are isolated by filtration.

The methods for the preparation of substantially crystalline material described herein constitute a further aspect of the present invention.

(E)-2-(5-Chlorothien-2-yl)-N-{(3S)-1-[(1S)-1-methyl-2-morpholin-4-yl-2-oxoethyl]-2-oxopyrrolidin-3-yl}ethenesulfonamide is a Factor Xa inhibitor and as such is useful in the treatment of clinical conditions susceptible to amelioration by administration of a Factor Xa inhibitor. Such conditions include acute vascular diseases such as acute coronary syndromes (for example primary and secondary prevention of myocardial infarction and unstable angina and treatment of prothrombotic sequalae associated with myocardial infarction or heart failure), thromboembolism, acute vessel closure associated with thrombolytic therapy and percutaneous transluminal coronary angioplasty (PTCA), transient ischemic attacks, pulmonary embolism, deep vein thrombosis, peripheral arterial occlusion, prevention of vessel luminal narrowing (restenosis), and the prevention of thromboembolic events associated with atrial fibrillation, e.g. stroke; treatment of ischemic stroke; in preventing thrombosis and complications in patients genetically predisposed to arterial thrombosis or venous thrombosis and patients that have a disease-associated predisposition to thrombosis (e.g. type 2 diabetics); the treatment of pulmonary fibrosis; the treatment of tumour metastasis; the treatment of inflammation; atherosclerosis; neurogenerative disease such as Parkinson's and Alzheimer's diseases; Kasabach Merritt Syndrome; Haemolytic uremic syndrome; endothelial dysfunction; as anti-coagulants for extracorporeal blood in for example, dialysis, blood filtration, bypass, and blood product storage;

and in the coating of invasive devices such as prostheses, artificial valves and catheters in reducing the risk of thrombus formation.

Accordingly, one aspect of the present invention provides (E)-2-(5-chlorothien-2-yl)-N-{(3S)-1-[(1S)-1-methyl-2-morpholin-4-yl-2-oxoethyl]-2-oxopyrrolidin-3-yl}ethenesulfonamide in substantially crystalline form for use in medical therapy, particularly for use in the amelioration of a clinical condition in a mammal, including a human, for which a Factor Xa inhibitor is indicated.

In another aspect, the invention provides a method for the treatment and/or prophylaxis of a mammal, including a human, suffering from a condition susceptible to amelioration by a Factor Xa inhibitor which method comprises administering to the subject an effective amount of (E)-2-(5-chlorothien-2-yl)-N-{(3S)-1-[(1S)-1-methyl-2-morpholin-4-yl-2-oxoethyl]-2-oxopyrrolidin-3-yl}ethenesulfonamide in substantially crystalline form.

In another aspect, the present invention provides the use of (E)-2-(5-chlorothien-2-yl)-N-{(3S)-1-[(1S)-1-methyl-2-morpholin-4-yl-2-oxoethyl]-2-oxopyrrolidin-3-yl}ethenesulfonamide in substantially crystalline form, for the manufacture of a medicament for the treatment and/or prophylaxis of a condition susceptible to amelioration by a Factor Xa inhibitor.

Preferably, the condition susceptible to amelioration by a Factor Xa inhibitor is selected from treatment of acute vascular diseases such as coronary thrombosis (for example myocardial infarction and unstable angina), thromboembolism, acute vessel closure associated with thrombolytic therapy and percutaneous transluminal coronary angioplasty, transient ischemic attacks, pulmonary embolism, deep vein thrombosis, peripheral arterial occlusion, prevention of vessel luminal narrowing (restenosis), and the prevention of thromboembolic events associated with atrial fibrillation, e.g. stroke.

More preferably, the condition susceptible to amelioration by a Factor Xa inhibitor is selected from coronary thrombosis (for example myocardial infarction and unstable angina), pulmonary embolism, deep vein thrombosis and the prevention of thromboembolic events associated with atrial fibrillation, e.g. stroke.

It will be appreciated that reference to treatment includes acute treatment or prophylaxis as well as the alleviation of established symptoms.

While it is possible that, for use in therapy, (E)-2-(5-chlorothien-2-yl)-N-{(3S)-1-[(1S)-1-methyl-2-morpholin-4-yl-2-oxoethyl]-2-oxopyrrolidin-3-yl}ethenesulfonamide in substantially crystalline form may be administered as the raw chemical, it is preferable to present the active ingredient as a pharmaceutical formulation.

In a further aspect, the invention provides a pharmaceutical composition comprising (E)-2-(5-chlorothien-2-yl)-N-{(3S)-1-[(1S)-1-methyl-2-morpholin-4-yl-2-oxoethyl]-2-oxopyrrolidin-3-yl}ethenesulfonamide in substantially crystalline form in association with a pharmaceutically acceptable carrier and/or excipient. The carrier and/or excipient must be "acceptable" in the sense of being compatible with the other ingredients of the formulation and not deleterious to the receipient thereof.

Accordingly, the present invention further provides a pharmaceutical formulation comprising (E)-2-(5-chlorothien-2-yl)-N-{(3S)-1-[(1S)-1-methyl-2-morpholin-4-yl-2-oxoethyl]-2-oxopyrrolidin-3-yl}ethenesulfonamide in substantially crystalline form, in association with a pharmaceutically acceptable carrier and/or excipient. The carrier and/or excipient must be "acceptable" in the sense of being compatible with the other ingredients of the formulation and not deleterious to the receipient thereof.

In another aspect, the invention provides a pharmaceutical composition comprising, as active ingredient, (E)-2-(5-chlorothien-2-yl)-N-{(3S)-1-[(1S)-1-methyl-2-morpholin-4-yl-2-oxoethyl]-2-oxopyrrolidin-3-yl}ethenesulfonamide in substantially crystalline form in association with a pharmaceutically acceptable carrier and/or excipient for use in therapy, and in particular in the treatment of human or animal subjects suffering from a condition susceptible to amelioration by a Factor Xa inhibitor.

There is further provided by the present invention a process of preparing a pharmaceutical composition, which process comprises mixing (E)-2-(5chlorothien-2-yl)-N-{(3S)-1-[(1S)-1-methyl-2-morpholin-4-yl-2-oxoethyl]-2-oxopyrrolidin-3-yl}ethenesulfonamide in substantially crystalline form, together with a pharmaceutically acceptable carrier and/or excipient.

(E)-2-(5-Chlorothien-2-yl)-N-{(3S)-1-[(1S)-1-methyl-2-morpholin-4-yl-2-oxoethyl]-2-oxopyrrolidin-3-yl}ethenesulfonamide in substantially crystalline form may be formulated for oral, buccal, parenteral, topical, rectal or transdermal administration or in a form suitable for administration by inhalation or insufflation (either through the mouth or the nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions or they may be presented as a dry product for constitution with water or other suitable vehicles before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound using a pharmaceutically acceptable carrier and/or excipients, e.g. hydroxypropyl methylcellulose.

For buccal administration the compositions may take the form of tablets or lozenges formulated in a conventional manner.

The compounds according to the present invention may be formulated for parenteral administration by injection, e.g. by bolus injection or continuous infusion. Formulations for injection may be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds according to the present invention may be formulated for topical administration by insufflation and inhalation. Examples of types of preparation for topical administration include sprays and aerosols for use in an inhaler or insufflator.

Powders for external application may be formed with the aid of any suitable powder base, for example, lactose, talc or starch. Spray compositions may be formulated as aqueous solutions or suspensions or as aerosols delivered from pressurised packs, such as metered dose inhalers, with the use of a suitable propellant.

The compounds according to the present invention may also be formulated in rectal compositions such as suppositories or retention enemas, e.g. containing conventional suppository bases such as cocoa butter or other glycerides.

In addition to the formulations described previously, the compounds may also be formulated as a depot preparation. Such long acting formulations may be administered by implantation (for example subcutaneously, transcutaneously or intramuscularly) or by intramuscular injection. Thus, for example, the compounds according to the present invention may be formulated with suitable polymeric or hydrophobic materials (for example as an emulsion in an acceptable oil) or ion exchange resins or as sparingly soluble derivatives, for example, as a sparingly soluble salt.

A proposed dose of (E)-2-(5-chlorothien-2-yl)-N-{(3S)-1-[(1S)-1-methyl-2-morpholin-4-yl-2-oxoethyl]-2-oxopyrrolidin-3-yl}ethenesulfonamide in substantially crystalline form according to the present invention for administration to a human (of approximately 70kg body weight) is 0.1 mg to 1 g, preferably to 1 mg to 500 mg of the active ingredient per unit dose, expressed as the weight of free base. The unit dose may be administered, for example, 1 to 4 times per day. The dose will depend on the route of administration. It will be appreciated that it may be necessary to make routine variations to the dosage depending on the age and weight of the patent as well as the severity of the condition to be treated. The dosage will also depend on the route of administration. The precise dose and route of administration will ultimately be at the discretion of the attendant physician or veterinarian.

(E)-2-(5-Chlorothien-2-yl)-N-{(3S)-1-[(1S)-1-methyl-2-morpholin-4-yl-2-oxoethyl]-2-oxopyrrolidin-3-yl}ethenesulfonamide in substantially crystalline form may also be used in combination with other therapeutic agents. The invention thus provides, in a further aspect, a combination comprising (E)-2-(5chlorothien-2-yl)-N-{(3S)-1-[(1S)-1-methyl-2-morpholin-4-yl-2-oxoethyl]-2-oxopyrrolidin-3-yl}ethenesulfonamide in substantially crystalline form together with a further therapeutic agent.

When (E)-2-(5-chlorothien-2-yl)-N-{(3S)-1-[(1S)-1-methyl-2-morpholin-4-yl-2-oxoethyl]-2-oxopyrrolidin-3-yl}ethenesulfonamide in substantially crystalline form is used in combination with a second therapeutic agent active against the same disease state the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the patient and will be ultimately at the discretion of the attendant physician or veterinarian. (E)-2-(5-Chlorothien-2-yl)-N-{(3S)-1-[(1S)-1-methyl-2-morpholin-4-yl-2-oxoethyl]-2-oxopyrrolidin-3-yl}ethenesulfonamide in substantially crystalline form may be used in combination with other antithrombotic drugs (such as thrombin inhibitors, thromboxane receptor antagonists, prostacyclin mimetics, phosphodiesterase inhibitors, fibrinogen antagonists, thrombolytic drugs such as tissue plasminogen activator and streptokinase, non-steroidal anti-inflammatory drugs such as aspirin, and the like), anti-hypertensive agents (such as angiotensin-converting enzyme inhibitors, angiotensin-II receptor antagonists, ACE/NEP inhibitors, β-blockers, calcium channel blockers, PDE inhibitors, aldosterone blockers), anti-atherosclerotic/dyslipidaemic agents (such as HMG-CoA reductase inhibitors) and anti-arrhythmic agents.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations by any convenient route.

When administration is sequential, either the Factor Xa inhibitor or the second therapeutic agent may be administered first. When administration is simultaneous, the combination may be administered either in the same or different pharmaceutical composition.

When combined in the same formulation it will be appreciated that the two compounds must be stable and compatible with each other and the other components of the formulation. When formulated separately they may be provided in any convenient formulation, conveniently in such manner as are known for such compounds in the art.

The present invention will now be further illustrated by the accompanying examples which should not be construed as limiting the scope of the invention in any way.

All publications, including but not limited to patents and patent applications, cited in this specification are herein incorporated by reference as if each individual publication were specifically and individually indicated to be incorporated by reference herein as though fully set forth.

EXAMPLES

Abbreviations
API Active Pharmaceutical Ingredient
DCM Dichloromethane
DMF N,N-Dimethylformamide
HOBT 1-Hydroxybenzotriazole
GC Gas Chromatography
LOD Loss On Drying
PAR Peak Area Ratio Intermediate 1 tert-Butyl N-[(benzyloxy)carbonyl]-L-methionyl-L-alaninate

Z-Protected L-methionine (10 g) was dissolved in DMF (200 ml) and 1-[3-(dimethylamino)propyol]-3-ethylcarbodiimide hydrochloride (8.13 g) was added followed by HOBT (5.72 g) and triethylamine (19.7 ml). The mixture was stirred for 1 h then L-alanine tert-butyl ester (7.7 g) was added and stirring continued for 18 h. The mixture was concentrated under reduced pressure and partitioned between diethyl ether and water. The separated organic phase was washed with hydrochloric acid (1M), saturated sodium bicarbonate solution and brine, dried (over magnesium sulphate) and concentrated under reduced pressure to give the title compound (11.9 g) as an orange oil which crystallised on standing.

Mass spectrum: Found: $MH^+$ 411.

Intermediate 2 tert-Butyl (2S)-2-((3S)-3-{[(benzyloxy)carbonyl]amino}-2-oxopyrrolidin-1-yl)propanoate A solution of Intermediate 1 (11.9 g) in acetone (75 ml) was treated with methyl iodide (18 ml) and stirred at room temperature for 72 h. The reaction mixture was then concentrated under reduced pressure to give an orange solid which was dissolved in acetonitrile (200 ml). Dowex (OH⁻ form) resin (19.42 g) was added and the mixture stirred for 18 h at room temperature. The mixture was filtered and the resin washed with ethyl acetate. The filtrate was concentrated under reduced pressure to afford a yellow oil which was purified by Biotage™ chromatography (eluting with cyclohexane:ethyl acetate 3:2) to give the title compound (2.92 g) as a colourless oil.

Mass spectrum: Found: MH$^+$ 363.

Intermediate 3

(2S)-2-((3S)-3-{[(Benzyloxy)carbonyl]amino}-2-oxopyrrolidin-1-yl)propanoic acid Intermediate 2 (0.5 g) was dissolved in DCM (7 ml), and trifluoroacetic acid (4.7 ml) was added. The mixture was stirred at room temperature for 1.5 h and then concentrated under reduced pressure to give the title compound (0.423 g) as a colourless oil which after azeotroping with toluene, crystallised.

Mass spectrum: Found: MH$^+$ 307.

Intermediate 4

Benzyl(3S)-1-[(1S)-1-methyl-2-morpholin-4-yl-2-oxoethyl]-2-oxopyrrolidin-3-ylcarbamate Intermediate 3 (84.5 g) was dissolved in DMF (2 l) and O-(benzotriazol-1-yl)-N,N,N',N'-tetramethyluronium tetrafluoroborate (161 g) was added, followed by N,N-diisopropylethylamine (92 ml) and morpholine (46 ml). The mixture was stirred under nitrogen for 2.5 h, and saturated aqueous ammonium chloride was added. The mixture was stirred for 15 min then partitioned between water and ethyl acetate. The separated organic phase was washed with lithium chloride (10% by weight), followed by saturated sodium bicarbonate and brine. The organic layer was dried (over sodium sulphate) and concentrated under reduced pressure to give the title compound (65 g) as a yellow solid.

Mass spectrum: Found: MH$^+$ 376.

Intermediate 5

(3S)-3-Amino-1-[(1S)-1-methyl-2-morpholin-4-yl-2-oxoethyl]pyrrolidin-2-one

A mixture of Intermediate 4 (20 g), 10% palladium on carbon (2 g) and ethanol (1.3 l) was stirred under an atmosphere of hydrogen for 16 h. The reaction mixture was filtered through Celite™ and the filtrate was concentrated under reduced pressure to give the title compound (12.3 g) as a pale white oil.

$^1$H NMR (D$_4$MeOH): δ5.05(1H, dd), 3.59(9H, m), 3.37(2H, m), 2.42(1H, m), 1.75(1H, m), 1.30(3H, d) ppm.

Intermediate 6

(S)-3-amino-1-[(S)-1-methyl-2-morpholin-4-yl-2-oxo-ethyl]-pyrrolidin-2-one hydrochloride To slurry of Intermediate 4 (5 g, 0.013 mol, 1 equivalent) in ethanol (75 ml) and hydrochloric acid (2.2 ml, 0.026 mol, 2 equivalents) was added 20% palladium hydroxide on carbon 50% water wet (100 mg, 2 weight %). The slurry was stirred at room temperature under approximately 15-20 psi for approximately 3 hours. The mixture was filtered through celite. The cake was washed with acetonitrile (2×30 ml). The filtrate contained (S)-3-amino-1-[(S)-1-methyl-2-morpholin-4-yl-2-oxo-ethyl]-pyrrolidin-2-one hydrochloride (yield assumed 100%).

Example 1

(E)-2-(5-Chlorothien-2-yl)-N-{(3S)-1-[(1S)-1-methyl-2-morpholin-4-yl-2-oxoethyl]-2-oxopyrrolidin-3-yl}ethenesulfonamide (Method 1)

To a solution of Intermediate 5 (14.9 g) in anhydrous acetonitrile (750 ml) were added (E)-2-(5-chlorothien-2-yl)ethenesulfonyl chloride (16.5 g) in acetonitrile (250 ml) and pyridine (11 ml), and the mixture was stirred at room temperature for 72 h. Saturated ammonium chloride solution was added and the resultant mixture stirred at room temperature for 30 min. The mixture was concentrated under reduced pressure and the residue partitioned between chloroform and a 1:1 mixture of hydrochloric acid (2M) and water. The organic layer was washed with a 1:1 mixture of saturated sodium bicarbonate and water, and brine. The organic layer was isolated, dried (over magnesium sulphate) and concentrated under reduced pressure to give the title compound (19.3 g) as a white solid (substantially amorphous form).

Mass spectrum: Found: MH$^+$ 448. H.p.l.c. Rt 2.99 min $^1$H NMR (CDCl$_3$):δ7.48(1H, d), 7.08(1H, d), 6.90(1H, d), 6.55(1H, d), 5.12(1H, br.d), 5.06(1H, q), 3.96(1H, m), 3.70-3.48(9H, m), 3.35(1H, m), 2.62(1H, m), 2.05(1H, m), 1.34(3H, d) ppm.

Crystallisation of Example 1

Example 1 (33.3 g) was dissolved in acetone (350 ml) at 55° C., whilst stirring under nitrogen. Water (780 ml) was added dropwise and in portions over 3.5 h, during which the solution began to appear cloudy. The heat was removed and the solution left to reach room temperature over 2 h. The mixture was left for a further 18 h at room temperature in the absence of light. The resultant suspension was filtered, washed with cold water (200 ml), and then dried under vacuum at 30° C. over 24 h, to give the title compound as a white substantially crystalline solid.

The substantially crystalline material obtained was used as a seed to initiate crystallisation in a repeat crystallisation process (as described above) in which the seed was added after removing the heat to give the title compound (29.2 g) as a white substantially crystalline solid.

Melting point (by DSC): melting onset 163 to 165° C.

The substantially crystalline solid exists predominately as needle-shaped and lath-shaped particles, up to 250 microns in length, which form loose agglomerates.

Figure 1:
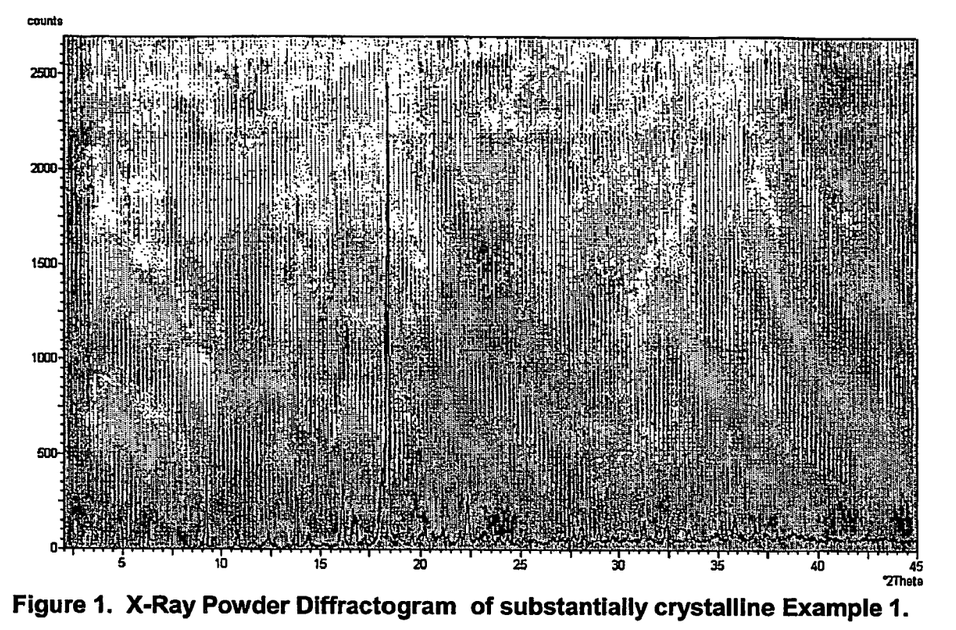
FIG. 1 shows the X-Ray Powder Diffractogram of substantially crystalline (E)-2-(5-Chlorothien-2-yl)-N-{(3S)-1-[(1S)-1-methyl-2-morpholin-4-yl-2-oxoethyl]-2-oxopyrrolidin-3-yl}ethenesulfonamide prepared according to Example 1.
Figure 2:
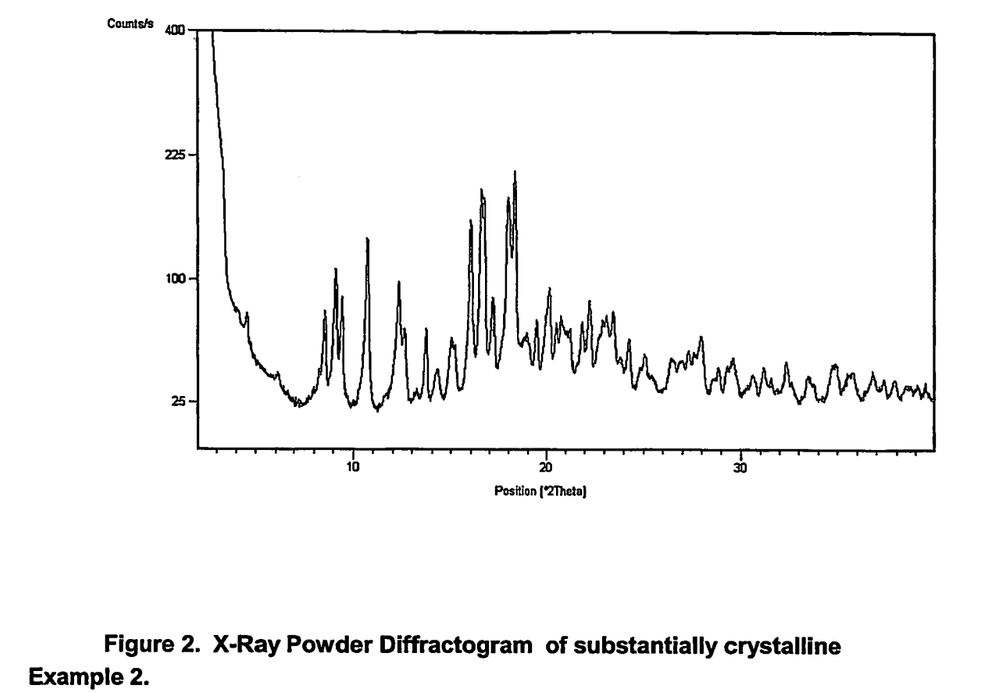
FIG. 2 shows the X-Ray Powder Diffractogram of substantially crystalline (E)-2-(5-Chlorothien-2-yl)-N-{(3S)-1-[(1S)-1-methyl-2-morpholin-4-yl-2-oxoethyl]-2-oxopyrrolidin-3-yl}ethenesulfonamide prepared according to Example 2.

The X-ray powder diffraction pattern of the crystalline compound as shown in FIG. 1 was obtained using the settings shown in Table 1. Table 2 lists characteristic peak data.

TABLE 1(a)

XRPD instrument details and measurement conditions

| | |
|---|---|
| Manufacturer | Philips Analytical X-Ray B.V. The Netherlands |
| Diffractometer type | PW3040 |
| Serial | DY667 |
| Tube Anode | Cu |
| LabdaAlpha 1 | 1.54056 |
| LabdaAlpha 2 | 1.54439 |
| Ratio Alpha21 | 0.50000 |
| Divergence slit | Prog. Div. Slit |
| Receiving slit | Prog. Rec. Slit |
| Monochromator used | YES |
| Generator voltage | 40 kV |
| Tube current | 50 mA |
| Data angle range (°2θ) | 2.0000-45.0000 |
| Scan step size (°2θ) | 0.020 |
| Scan type | Continuous |
| Scan step time | 1.00 seconds |

TABLE 1(b)

DSC for melting onset Instrument details and measurement conditions

| | | |
|---|---|---|
| Instrument | Manufacturer/Model: | TA Instruments DSC2920 |
| | Serial No. | M2920-234 |
| Method | Sample pre-treatment | None |
| | Purge gas identity/ flow rate | Nitrogen/20 ml min$^{-1}$ |
| | Sample pan type | Pinhole aluminium |
| | Heating rate | 10° C. min$^{-1}$ |
| | Temperature range | Ambient to 300° C. |

Melting onset for substantially crystalline material 163-165° C.

Microscopy

Particles described as acicular or lath shaped crystals up to 400 microns in length

TABLE 2

XRPD peak data for (E)-2-(5-chlorothien-2-yl)-N-{(3S)-1-[(1S)-1-methyl-2-morpholin-4-yl-2-oxoethyl]-2-oxopyrrolidin-3-yl}ethenesulfonamide in substantially crystalline form (Example 1); characterized by an X-ray powder diffraction pattern that contains but is not limited to the peaks in Table 2.

| Angle (°2θ) | d K-alpha1 (Å) | Relative Intensity (%) |
|---|---|---|
| 4.65 | 18.98 | 0.9 |
| 8.67 | 10.19 | 0.69 |
| 9.21 | 9.59 | 17.5 |
| 9.55 | 9.26 | 1.1 |
| 10.82 | 8.17 | 3.2 |
| 12.41 | 7.13 | 3.4 |
| 12.71 | 6.96 | 1.0 |
| 13.79 | 6.42 | 11.6 |
| 14.38 | 6.16 | 3.2 |
| 15.19 | 5.83 | 0.7 |
| 16.11 | 5.50 | 13.2 |
| 16.64 | 5.32 | 5.8 |
| 16.80 | 5.27 | 6.7 |
| 17.27 | 5.13 | 2.5 |
| 18.11 | 4.89 | 16.8 |
| 18.39 | 4.82 | 100.0 |
| 18.90 | 4.69 | 2.7 |
| 19.57 | 4.53 | 2.3 |
| 20.25 | 4.38 | 3.7 |

TABLE 2-continued

XRPD peak data for (E)-2-(5-chlorothien-2-yl)-N-{(3S)-1-[(1S)-1-methyl-2-morpholin-4-yl-2-oxoethyl]-2-oxopyrrolidin-3-yl}ethenesulfonamide in substantially crystalline form (Example 1); characterized by an X-ray powder diffraction pattern that contains but is not limited to the peaks in Table 2.

| Angle (°2θ) | d K-alpha1 (Å) | Relative Intensity (%) |
|---|---|---|
| 20.62 | 4.30 | 3.1 |
| 21.14 | 4.20 | 4.0 |
| 21.95 | 4.05 | 2.6 |
| 22.37 | 3.97 | 9.6 |

Example 2

(E)-2-(5-Chlorothien-2-yl)-N-{(3S)-1-[(1S)-1-methyl-2-morpholin-4-yl-2-oxoethyl]-2-oxopyrrolidin-3-yl}ethenesulfonamide (Method 2)

Stoichiometry of raw materials and reagents, and volumes (vol) of solvents used were calculated based on the amount of (S)-3-amino-1-[(S)-1-methyl-2-morpholin-4-yl-2-oxoethyl]-pyrrolidin-2-one hydrochloride which was assumed 100% yield from Intermediate 5.

(S)-3-Amino-1-[(S)-1-methyl-2-morpholin-4-yl-2-oxoethyl]-pyrrolidin-2-one hydrochloride (1.0 eq) (Intermediate 6) in ethanol and pyridine (3 volumes) was charged to the reactor, and then concentrated under vacuum below 40° C. to about 3 volumes. 10 volumes of acetonitrile was added, then the solution was concentrated under vacuum below 40° C. to about 3 volumes. The addition and concentration of acetonitrile were repeated (4 cycles) until acceptable level of ethanol was below 0.1% w/w (GC analysis for ethanol). The GC sample was taken between 4th and 5th cycles after addition of 10 vol acetonitrile.

The volumes of (S)-3-amino-1-[(S)-1-methyl-2-morpholin-4-yl-2-oxo-ethyl]-pyrrolidin-2-one hydrochloride solution were adjusted to about 13 volumes with acetonitrile (roughly pyridine, 3 vol; acetonitrile, 10 vol) at ambient temperature. (E)-2-(5-Chloro-thiophen-2-yl)-ethenesulfonyl chloride (1.0-1.4 eq) was charged as solid in one portion into the reactor. The mixture was stirred at ambient temperature until reaction was complete, monitoring by HPLC (Note: the reaction was considered complete when HPLC analysis showed that the ratio of (E)-2-(5chlorothien-2-yl)-N-{(3S)-1-[(1S)-1-methyl-2-morpholin-4-yl-2-oxoethyl]-2-oxopyrrolidin-3-yl}ethenesulfonamide: (E)-2-(5-chloro-thiophen-2-yl)-ethenesulfonyl chloride (plus acid from (E)-2-(5-chloro-thiophen-2-yl)-ethenesulfonyl chloride) was greater than 86:14 PAR). Butyl acetate (15 vol) was added to reaction mixture. Solvents were removed by distillation under vacuum below 70° C. until about 12-13 vol. Water (10 vol) was added and stirred at approximately 70° C. for 30-60min to ensure that all oily materials were dissolved. The mixture was settled for about 30 min and separated. The organic phase was washed with water (5 vol) at 60-70° C. The combined aqueous phases were extracted with butyl acetate (15 vol) at approximately 60° C. The combined organic phases were filtered at 50-60° C. (final API) and then concentrated to approximately 10 vol under vacuum <80° C. Solid precipitates out during concentration. The slurry was cooled to ambient temperature. Cyclohexane (10 vol, filtered) was added and the slurry was held for 4-24 h. The solid was filtered and washed with cyclohexane (10 vol, filtered). The product was dried at 60-70° C. under vacuum until consistent weight or LOD <0.5% at 125° C. for 5 min to afford off-white solid. Yield range observed: 60-70%

Crystallisation of Example 2

(E)-2-(5-Chlorothien-2-yl)-N-{(3S)-1-[(1S)-1-methyl-2-morpholin-4yl-2-oxoethyl]-2-oxopyrrolidin-3-yl}ethenesulfonamide (29.25 g) was suspended in n-propanol (225 mL, 7.5 volumes). The suspension was heated to 75° C. The solution was then filtered hot. Cyclohexane (225 mL, 7.5 volumes) was added and the mixture heated to reflux (74° C.). The solution was then cooled to around 65° C. and seeds (0.2% w/w in cyclohexane) were added. The resultant slurry was held at 65° C. for 30 minutes after the onset of crystallization. The content was cooled to 0-5° C. (cooling rate, 0.5° C./min). The suspension was stirred at 0-5° C. for 1 hour and filtered under vacuum. The cake was then washed with cyclohexane (150 mL, 5.0 volumes) and set in a vacuum oven (60° C./25 mmHg) to dry to constant weight. Weight of (E)-2-(5-chlorothien-2-yl)-N-{(3S)-1[(1S)-1-methyl-2-morpholin-4-yl-2-oxoethyl]-2-oxopyrrolidin-3-yl}ethenesulfonamide was 24.7 g (85%). Percent yield range observed: 85-90% of a light yellow solid.

TABLE 3

XRPD instrument details and measurement conditions

| | |
|---|---|
| Manufacturer | Philips Analytical |
| Diffractometer type | X'Pert Pro MPD Diffractometer |
| Detector Type | X'Celerator RTMS (Real Time Multi Strip) |
| Tube Anode | Cu |
| LabdaAlpha 1 (Å) | 1.54056 |
| LabdaAlpha 2 (Å) | 1.54439 |
| Ratio Alpha21 | 0.50000 |
| Incident beam optics | fixed slits (0.5° aperture), 0.04 radian soller slits, 10 mm beam mask |
| Diffracted beam optics | fixed slits (X'celerator module), 0.04 radian soller slits |
| Generator voltage (kV) | 40 |
| Tube current (mA) | 40 |
| Data angle range (°2θ) | 2.0-40.0 |
| Scan step size (°2θ) | 0.017 |
| Scan type | Continuous |
| Scan step time (s) | 80 |
| Sample rotation (rpm) | 25 |

TABLE 4

XRPD peak data for (E)-2-(5-chlorothien-2-yl)-N-{(3S)-1-[(1S)-1-methyl-2-morpholin-4-yl-2-oxoethyl]-2-oxopyrrolidin-3-yl} ethenesulfonamide in substantially crystalline form (Example 2); characterized by an X-ray powder diffraction pattern that contains but is not limited to the peaks in Table 4.

| Angle (°2θ) | d K-alpha1 (Å) | Relative Intensity (%) |
|---|---|---|
| 4.5 | 19.5 | 21 |
| 8.6 | 10.3 | 22 |
| 9.1 | 9.7 | 38 |
| 9.4 | 9.4 | 28 |
| 10.7 | 8.3 | 53 |
| 12.3 | 7.2 | 34 |
| 12.6 | 7.0 | 16 |
| 13.7 | 6.5 | 17 |
| 16.0 | 5.5 | 66 |
| 16.6 | 5.3 | 86 |
| 16.7 | 5.3 | 77 |
| 17.2 | 5.2 | 27 |
| 18.0 | 4.9 | 81 |
| 18.3 | 4.8 | 100 |
| 19.5 | 4.6 | 19 |
| 20.2 | 4.4 | 31 |
| 20.5 | 4.3 | 18 |
| 21.9 | 4.1 | 19 |
| 22.3 | 4.0 | 27 |
| 22.9 | 3.9 | 19 |
| 23.1 | 3.8 | 20 |
| 23.5 | 3.8 | 22 |

What is claimed is:

1. (E)-2-(5-Chlorothien-2-yl)-N-{(3S)-1-[(1S)-1-methyl-2-morpholin-4-yl-2-oxoethyl]-2-oxopyrrolidin-3-yl}ethenesulfonamide in substantially crystalline form having an X-ray powder diffraction pattern expressed in terms of 2 theta angles and obtained with a diffractometer, wherein said X-ray powder diffraction pattern comprises 2 theta angles at one or more positions selected from the group consisting of 9.1-9.2 (±0.1), 16.0-16.1 (±0.1), 18.0-18.2 (±0.1), and 18.3-18.4 (±0.1) degrees.

2. The substantially crystalline form as claimed in claim 1 in the form of needle-shaped crystals.

3. The substantially crystalline form as claimed in claim 1 in the form of lath-shaped crystals.

4. The substantially crystalline form as claimed in claim 1 in the form of a mixture of needle-shaped and lath-shaped crystals.

5. The substantially crystalline form as claimed in claim 1 wherein the melting point is greater than 160° C.

6. The substantially crystalline form as claimed in claim 1 having an X-ray powder diffraction pattern expressed in terms of 2 theta angles and obtained with a diffractometer, wherein said X-ray powder diffraction pattern comprises 2 theta angles at two or more positions selected from the group consisting of 9.1-9.2 (±0.1), 16.0-16.1 (±0.1), 18.0-18.2 (±0.1), and 18.3-18.4 (±0.1) degrees.

7. The substantially crystalline form as claimed in claim 1 having an X-ray powder diffraction pattern expressed in terms of 2 theta angles and obtained with a diffractometer, wherein said X-ray powder diffraction pattern comprises 2 theta angles at three or more positions selected from the group consisting of 9.1-9.2 (±0.1), 16.0-16.1 (±0.1), 18.0-18.2 (±0.1), and 18.3-18.4 (±0.1) degrees.

8. The substantially crystalline form as claimed in claim 1 having an X-ray powder diffraction pattern expressed in terms of 2 theta angles and obtained with a diffractometer, wherein said X-ray powder diffraction pattern comprises 2 theta angles at all four positions selected from the group consisting of 9.1-9.2 (±0.1), 16.0-16.1 (±0.1), 18.0-18.2 (±0.1), and 18.3-18.4 (±0.1) degrees.

9. A method for the preparation of (E)-2-(5-chlorothien-2-yl)-N-{(3S)-1-[(1S)-1-methyl-2-morpholin-4-yl-2-oxoethyl]-2-oxopyrrolidin-3-yl}ethenesulfonamide in substantially crystalline form which method comprises crystallisation of (E)-2-(5-chlorothien-2-yl)-N-{(3S)-1-[(1S)-1-methyl-2-morpholin-4-yl-2-oxoethyl]-2-oxopyrrolidin-3-yl}ethenesulfonamide from an organic solution, optionally in the presence of water.

10. A method as claimed in claim 9 wherein the organic solution selected from: an aromatic hydrocarbon, a cycloalkane, an ester, an alcohol or a ketone, or a mixture thereof.

* * * * *